US007243554B2

(12) United States Patent
Wenski (10) Patent No.: US 7,243,554 B2
(45) Date of Patent: *Jul. 17, 2007

(54) MICRO-TENSILE TESTING SYSTEM (75) Inventor: Edward G. Wenski, Lenexa, KS (US)

(73) Assignee: Honeywell Federal Manufacturing & Technologies, Kansas City, MO (US)

( * ) Notice: Subject to any disclaimer, the term of this patent is extended or adjusted under 35 U.S.C. 154(b) by 96 days.

This patent is subject to a terminal disclaimer.

(21) Appl. No.: 11/229,111

(22) Filed: Sep. 16, 2005

(65) Prior Publication Data

US 2006/0010986 A1 Jan. 19, 2006

Related U.S. Application Data

(63) Continuation of application No. 10/412,508, filed on Apr. 11, 2003, now Pat. No. 6,983,658.

(51) Int. Cl.
*G01L 1/24* (2006.01)
(52) U.S. Cl. ....................................................... 73/800
(58) Field of Classification Search ................... 73/800
See application file for complete search history.

(56) References Cited

U.S. PATENT DOCUMENTS 5,741,976 A   4/1998   Schinke et al.
6,370,962 B1 *  4/2002   Sullivan et al. ............... 73/826

OTHER PUBLICATIONS

Read, D.T., "Piezo-Actuated Microtensile Test Apparatus", *Journal of Testing and Evaluation*. vol. 26 No. 3, May 1998.
Ilzhofer et al., "Tensile Testing Device for Microstructured Specimens", *Microsystems Technologies* Dec. 4, 1997.
Ogawa et al., "A Tensile Testing Method for Small-Sized Materials", *Journal of Mechanical Engineering Laboratory* Vo. 49 No. 2, Mar. 1995.

* cited by examiner

*Primary Examiner*—Michael Cygan
*Assistant Examiner*—Octavia Davis
(74) *Attorney, Agent, or Firm*—Hovey Williams LLP (57) ABSTRACT

A micro-tensile testing system providing a stand-alone test platform for testing and reporting physical or engineering properties of test samples of materials having thicknesses of approximately between 0.002 inch and 0.030 inch, including, for example, LiGA engineered materials. The testing system is able to perform a variety of static, dynamic, and cyclic tests. The testing system includes a rigid frame and adjustable gripping supports to minimize measurement errors due to deflection or bending under load; serrated grips for securing the extremely small test sample; high-speed laser scan micrometers for obtaining accurate results; and test software for controlling the testing procedure and reporting results.

22 Claims, 6 Drawing Sheets

MICRO-TENSILE TESTING SYSTEM

RELATED APPLICATIONS

The present application is a continuation and claims priority of a co-pending application titled "MICRO-TENSILE TESTING SYSTEM", Ser. No. 10/412,508, filed Apr. 11, 2003 now U.S. Pat. No. 6,983,658, the content of which is hereby incorporated by reference.

FEDERALLY SPONSORED RESEARCH OR DEVELOPMENT PROGRAM

The U.S. Government has a paid-up license in this invention and the right in limited circumstances to require the patent owner to license others on reasonable terms as provided for by the terms of Contract No. DE-AC04-01AL66850 awarded by the U.S. Department of Energy.

BACKGROUND OF THE INVENTION

1. Field of the Invention

The present invention relates broadly to systems and apparatuses for measuring, determining, or otherwise testing physical or engineering properties of materials. More particularly, the present invention concerns a micro-tensile testing system providing a stand-alone test platform for testing and reporting physical or engineering properties of test samples of materials having thicknesses of approximately between 0.002 inch and 0.030 inch, including, for example, LiGA engineered materials, wherein the testing system is able to perform a variety of static, dynamic, and cyclic tests, and includes serrated grips for securing the test sample, dual high-speed laser scan micrometers for obtaining accurate results, and test software for controlling the testing procedure and reporting results.

2. Description of the Prior Art

It is often desirable to measure, determine, or otherwise test physical or engineering properties of test samples of materials, including such properties as modulus of elasticity, yield strength, ultimate strength, failure strength, and elongation at failure. To accomplish such testing and measuring, a variety of prior art testing systems and techniques have been developed. Unfortunately, these prior art testing systems and techniques, while suitable for testing larger test samples, are unsuitable for testing extremely small test samples, such as, for example, test samples of materials engineered using a lithographic electroplating formation (LiGA) process. Prior art testing systems are often unable to accommodate and secure test samples smaller than approximately 0.030 inch, particularly when substantial force is applied to the test sample during testing.

Furthermore, the frames or structural support members of prior art testing systems often suffer from substantial deflection or bending during testing, particularly under high loading, which can result in increased measurement errors. Additionally, prior art testing systems typically employ tangible extensometers to measure displacement. Unfortunately, while suitable for use with larger test samples, tangible extensometers can significantly distort test results when used with smaller test samples. Additionally, prior art testing systems often require substantial labor-intensive work by the user in the form of calibration, test control, data acquisition, and data manipulation and analysis, all of which can substantially increase error risks.

Due to the above-identified and other problems and disadvantages in the art, a need exists for an improved testing system.

SUMMARY OF THE INVENTION

The present invention overcomes the above-described and other problems and disadvantages in the prior art with an micro-tensile testing system providing a stand-alone test platform for measuring, determining, or otherwise testing and reporting physical or engineering properties of a test sample of a material having a thickness of approximately between 0.002 inch and 0.03 inch. The testing system is able to perform both static and dynamic tests, including, for example, tensile, compression, flex, and shear, and cyclic tests to measure or determine such properties as modulus of elasticity, yield strength, ultimate strength, failure strength, and elongation at failure. The test sample can be of substantially any micromachinable material, including, for example, materials engineered using a LiGA process.

In a preferred embodiment, the testing system broadly comprises a frame; upper and lower linear bearings; upper and lower gripping supports; upper and lower serrated grips; a connecting or drive rod; a drive mechanism; a microstepping drive and a keypad; two or more laser micrometers; a laser display monitor; a plurality of load cells; a load cell indicator; and digital acquisition hardware, including a connector block and a data acquisition computer card; a computing device; and test software.

The frame is adapted to securely support and retain other components of the testing system, and to provide sufficient rigidity to allow for exerting substantial force on the test sample without unduly affecting measurement error rate. Furthermore, the frame is designed such that the test sample is precisely aligned so that all forces are evenly distributed on the frame, thereby further advantageously minimizing deflection or bending of the frame during testing.

The upper and lower linear bearings are attached to the frame and adapted to carry the upper and lower gripping supports. The linear bearings have low profiles and include two linear rails whereupon ride two frictionless guide carriages to which the gripping supports are attached. The guide carriages advantageously eliminate rotation effects and minimize damage to the test sample during installation.

The upper and lower gripping supports are each coupled with a respective one of the linear bearings and are adapted to support the test sample during testing. Interchangeable metal inserts or shims can be used to align or otherwise accommodate testing samples having thicknesses of approximately between 0.002 inch and 0.030 inch. The upper and lower serrated grips are adapted to further facilitate securing the test sample during testing, and may be implemented as serrated faces attached with screws or other suitable fasteners to the gripping supports.

The connecting or drive rod extends between the gripping supports and the drive mechanism and is adapted to allow for quickly and efficiently accommodating test samples of various overall sizes, particularly samples having various overall lengths.

The drive mechanism is adapted to apply a load to the gripping supports. Preferably, the drive mechanism includes an electric drive and a gearbox cooperating to provide both a desired degree of linear travel and test speed control. The microstepping drive and the keypad are adapted to allow for conditioning and controlling the drive mechanism. More specifically, the microstepping drive allows for detailed control of the displacement of the electric drive, including controlling the application of force from approximately between 0.0002 inch per minute and 0.2500 inch per minute. The microstepping drive also allows for constant loading for testing the tensile strength of the test sample. The keypad provides an input device adapted to allow for more convenient user control of the microstepping drive and the testing regime.

The first and second laser micrometers are adapted to detect and record an extension, elongation, or displacement change of the test sample during testing. The dual laser micrometers provide independent measurements of the overall length of the gage section of the test sample which are used to calculate an average strain on the test sample. Such averaging substantially reduces or eliminates a bending component of the strain and provides a more accurate result than if only one measurement was used, as is the case in the prior art. Preferably, the laser micrometers are high-speed laser scan micrometers. Use of the laser micrometers, rather than the tangible extensometers used in the prior art, advantageously eliminates a potential source of test data distortion. The laser display monitor is adapted to condition and display the two independently measured overall lengths of the gage section of the test sample, and to output these values on separate displacement channels to the computing device where they are averaged by the test software.

The plurality of load cells are adapted to record loading on the test sample during testing. Preferably, there are at least four interchangeable load cells, with each having full-scale load ratings of 25 lbs, 50 lbs, 100 lbs, and 250 lbs, which advantageously allows for greater testing flexibility. The load cell indicator is adapted to facilitate verification and calibration of the load cells. In one embodiment, the load cell indicator is a strain gage conditioner adapted to apply a regulated DC voltage to each of the load cells, display the applied load, and output the load signal for digital data recording.

The digital acquisition hardware is adapted to control both calibration and digital data recording of the test signal. The acquisition hardware includes the connector block which is attached to the data acquisition computer card which is, in turn, operatively coupled with or incorporated into the computing device. The computing device is conventionally operable to store and execute the test software and to receive and report test data. The computing device broadly includes a memory and a processor, with the memory being operable to store the test software and the test data, and the processor being operable to execute the test software and to receive the test data.

The test software is adapted to facilitate and control the testing process by, for example, facilitating calibration of the testing system via a user interface; controlling the forces applied and measurements made by the drive mechanism, measuring devices (e.g., the laser micrometers), and other components of the testing system; and acquiring test data via the connector block and the data acquisition computer card. The test software also functions to communicate or report various test parameters or results, including, for example, load, stress, strain, test time, maximum stress, and two-dimensional X-Y or three-dimensional X-Y-Z plots of the test data in real-time mode.

Thus, it will be appreciated that the testing system of the present invention provides a number of substantial advantages over the prior art, including, for example, advantageously accommodating test samples between approximately 0.002 inch and 0.030 inch in size. Furthermore, the extreme rigidity of the frame and adjustability of the gripping supports advantageously facilitates minimizing errors due to deflection of bending during testing. Additionally, the serrated grips advantageously facilitate securing the extremely small test samples during testing. Additionally, the laser micrometers advantageously minimize measurement errors experienced by prior art testing systems using tangible extensometers. Additionally, integration of the testing software into the testing system advantageously minimizes labor-intensive user work and user error by giving primary control of calibration, testing, data acquisition, and data manipulation and analysis to the computer program.

These and other important features of the present invention are more fully described in the section titled DETAILED DESCRIPTION OF A PREFERRED EMBODIMENT, below.

BRIEF DESCRIPTION OF THE DRAWINGS

A preferred embodiment of the present invention is described in detail below with reference to the attached drawing figures, wherein.

DETAILED DESCRIPTION OF A PREFERRED EMBODIMENT

Referring to FIGS. 1-4, a micro-tensile testing system 10 is shown constructed in accordance with a preferred embodiment of the present invention. The testing system 10 provides a stand-alone test platform for measuring, determining, or otherwise testing and reporting physical or engineering properties of a test sample 11 (see FIG. 4) of a material having a thickness of approximately between 0.002 inch and 0.030 inch. The testing system 10 is able to perform both static and dynamic tests, including, for example, tensile, compression, flex, and shear, and cyclic tests to measure or determine such properties as modulus of elasticity, yield strength, ultimate strength, failure strength, and elongation at failure. The test sample 11 can be of substantially any micromachinable material, including, for example, materials engineered using a LiGA process.

In a preferred embodiment, the testing system 10 broadly comprises a frame 12; upper and lower linear bearings 14A, 14B; upper and lower gripping supports 16A, 16B; upper and lower serrated grips 18A, 18B; a connecting or drive rod 20; a drive mechanism 22; a microstepping drive 24 and a keypad 26; two or more laser micrometers 28A, 28B; a laser display monitor 30; a plurality of load cells 32; a load cell indicator (not shown); and digital acquisition hardware 36, including a connector block 38 and a data acquisition computer card 40; a computing device 42; and test software.

Figure 1:
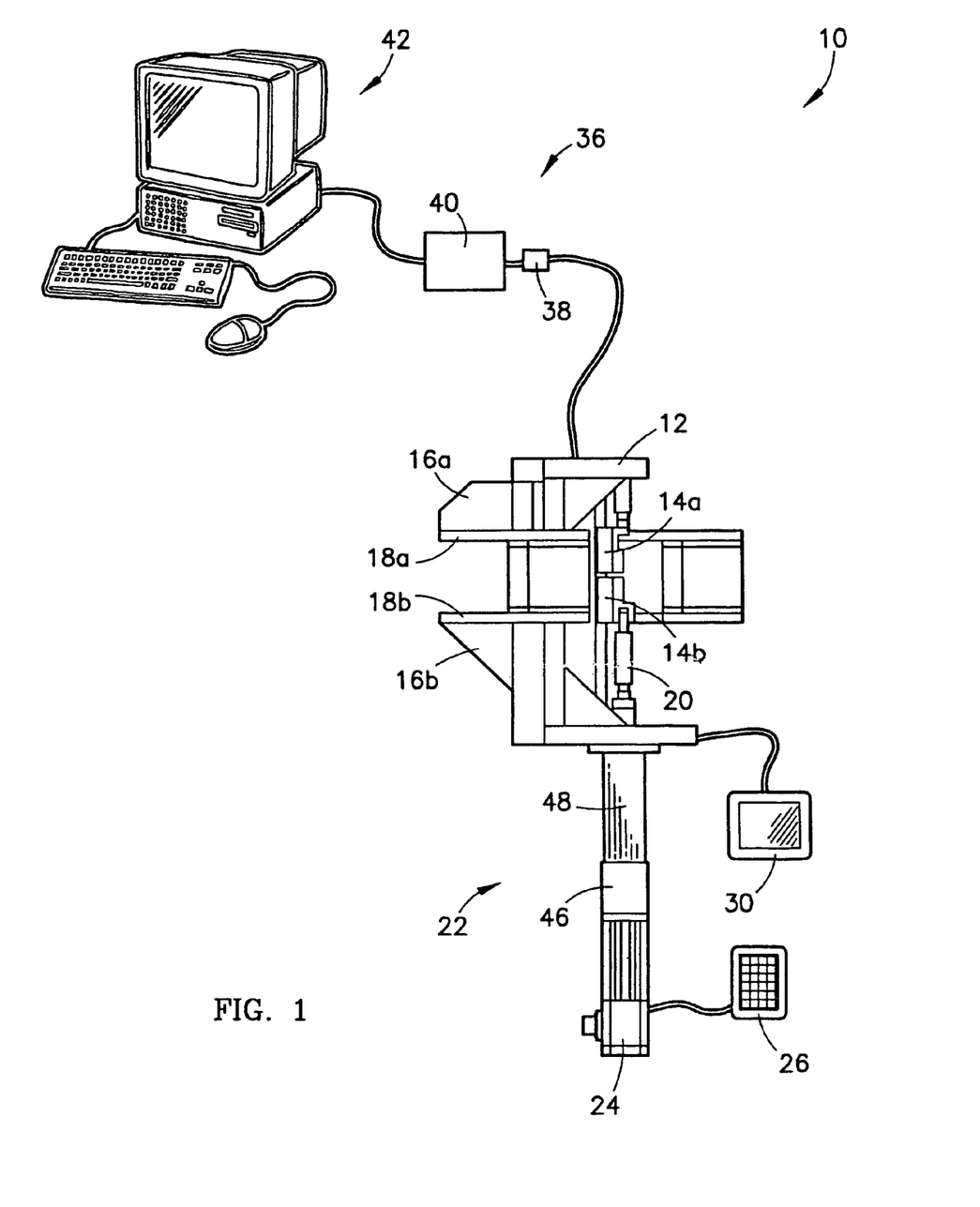
FIG. 1 is a right side elevational view of a preferred embodiment of a testing system of the present invention.
Figure 2:
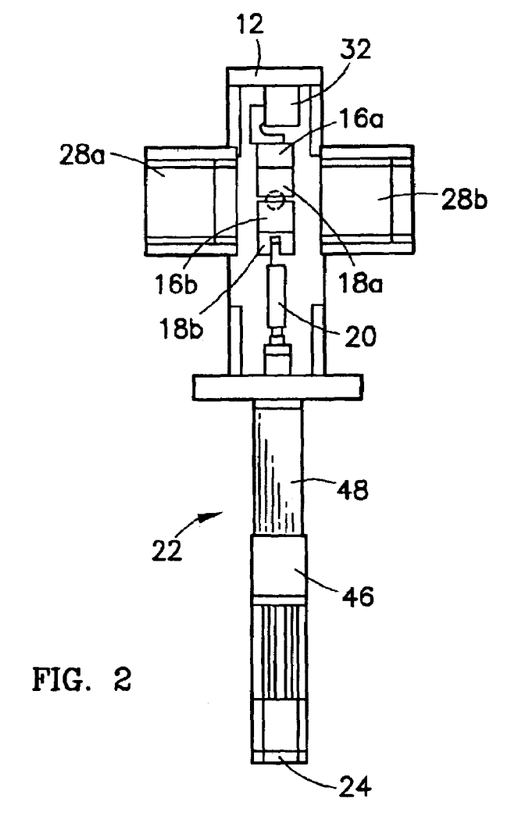
FIG. 2 is a front elevational view of the testing system of FIG. 1.
Figure 3:
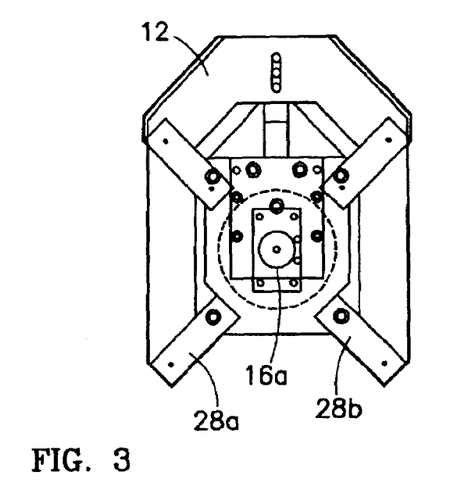
FIG. 3 is a plan view of the testing system of FIG. 1.

The frame 12 is adapted to securely support and retain other components of the testing system 10, and to provide sufficient rigidity to allow for exerting substantial force on the test sample 11 without unduly affecting measurement error rate. In a preferred embodiment, the frame 12 is adapted to allow for exerting up to approximately 250 pounds of axial load on the test sample 11 with minimal error in the test results (a 1% error rate). To accomplish this, the frame 12 is preferably constructed of flat ground tool steel and designed such that, during testing, the test sample is precisely aligned so that all forces are evenly distributed on the frame 12, thereby advantageously minimizing deflection or bending of the frame 12 during testing.

The upper and lower linear bearings 14A, 14B are attached to the frame 12 and adapted to carry the upper and lower gripping supports 16A, 16B. The linear bearings 14A, 14B have low profiles and include two linear rails whereupon ride two frictionless guide carriages to which the gripping supports 16A, 16B are attached. The guide carriages advantageously eliminate rotation effects and minimize damage to the test sample 11 during installation. Suitable linear bearings 14A, 14B are available from a variety of suppliers, including, for example, Thomson Industries of Port Washington, N.Y.

Figure 4:
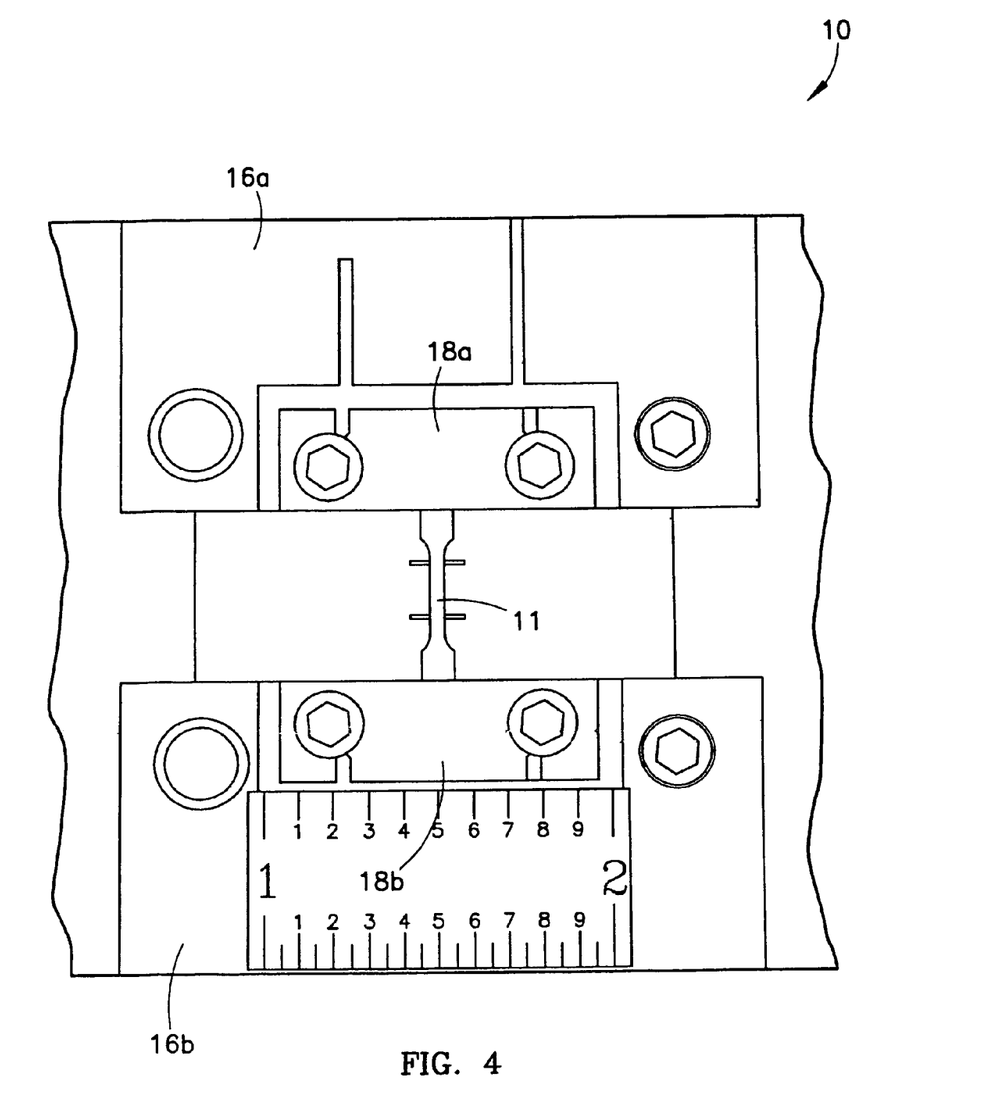
FIG. 4 is a fragmentary view of a portion of the testing system of FIG. 1 magnified to better show gripping support and serrated grip components.

The upper and lower gripping supports 16A, 16B are each coupled with a respective one of the linear bearings 14A, 14B and are adapted to support the test sample 11 during testing. The gripping supports 16A, 16B preferably each include an interchangeable metal insert or shim that facilitates maintaining alignment of the test sample 11 relative to the centerline of the frame 12, thereby advantageously further facilitating maintaining an even load distribution on the frame 12. A variety of metal inserts or shims can be used to align or otherwise accommodate testing samples having thicknesses of approximately between 0.002 inches and 0.030 inches. The upper and lower serrated grips 18A, 18B are adapted to further facilitate securing the test sample 11 during testing, particularly under high loads, and may be implemented as serrated faces attached with screws or other suitable fasteners to the gripping supports 16A, 16B. The gripping supports 16A, 16B can provide a stable base for additional fixturing as well.

The connecting or drive rod 20 extends between the gripping supports 16A, 16B and the drive mechanism 22 and is adapted to allow for quickly and efficiently accommodating test samples of various sizes, particularly samples having various overall lengths. In a preferred form, the connecting rod 20 is substantially similar to a turnbuckle.

The drive mechanism 22 is adapted to apply a load to the gripping supports 16A, 16B. Preferably, the drive mechanism 22 includes an electric drive 46 and a gearbox 48 cooperating to provide both a desired degree of linear travel and test speed control. The electric drive 46 preferably provides a two inch travel and a five pitch ball screw. The gearbox 48 preferably provides a 70-to-1 gearing ratio. The electric drive 46 and the gearbox 48 attach to a base portion of the frame 12 and apply loading to the bottom of the connecting rod 20. A suitable electric drive is available from a variety of suppliers, including, for example, as the N-Series of electric drives from Industrial Devices Company of Petaluma, Calif. Alternatively the drive mechanism 22 may include any suitable driving device or apparatus, such as, for example, a hydraulic or pneumatic drive.

The microstepping drive 24 and the keypad 26 are adapted to allow for conditioning and controlling the drive mechanism 22. More specifically, the microstepping drive 24 allows for detailed control of the displacement of the electric drive 46, including controlling the application of force from approximately between 0.0002 inch per minute and 0.2500 inch per minute. The microstepping drive 24 also allows for constant loading for testing the tensile strength of the test sample 11. A suitable microstepping drive is available from various suppliers, including, for example, as the model SmartStep Microstepping Drive from Industrial Devices Company of Petaluma, Calif. The keypad 26 provides an input device adapted to allow for more convenient user control of the microstepping drive 24 and the testing regime. Thus, the user can, during the test process, vary the application of force by using the keypad 26 to input new values to the microstepping drive 24.

The first and second laser micrometers 28A, 28B are adapted to detect and record an extension, elongation, or displacement change of the test sample 11 during testing. The dual laser micrometers 28A, 28B provide independent measurements of the overall length of the gage section of the test sample 11 which are used to calculate an average strain on the test sample 11. Such averaging substantially reduces or eliminates a bending component of the strain and provides a more accurate result than if only one measurement was used, as is the case in the prior art. Preferably, the laser micrometers 28A, 28B are high-speed laser scan micrometers. Use of the laser micrometers 28A, 28B, rather than the tangible extensometers used in the prior art, advantageously eliminates a potential source of test data distortion. Calibration of the laser micrometers 28A, 28B can be completed using various metal blanks with NIST tracability. Suitable laser micrometers are available from various suppliers, including, for example, as the Model LS-5041 from Keyence Corporation of Osaka, Japan.

The laser display monitor 30 is adapted to condition and display the extension of each side of the test sample 11 as detected by the laser micrometers 28A, 28B. The display monitor 30 preferably provides a numerical display of the overall length of the gage section of the test sample 11 as determined by the first laser micrometer 28A and of the overall length of the gage section of the test sample 11 as determined by the second laser micrometer 28B. The two independent measurements are output on separate displacement channels to the computing device 42 and averaged by the test software. A suitable display monitor is available from a variety of suppliers, including, for example, as the Series LS-5000 from Keyence Corporation of Osaka, Japan.

The plurality of load cells 32 are adapted to record the loading on the test sample 11 during testing. Preferably, there are at least four interchangeable load cells, with each having full-scale load ratings of 25 lbs, 50 lbs, 100 lbs, and 250 lbs, which advantageously allows for greater testing flexibility. Calibration of the load cells 32 is conducted with dead weight calibration with NIST tracability. Suitable load cells are available from a variety of suppliers, including, for example, as the SM series of load cells from Interface Inc. of Scottsdale, Ariz.

The load cell indicator is adapted to facilitate verification and calibration of the load cells 32. In one embodiment, the load cell indicator is a strain gage conditioner adapted to apply a regulated DC voltage to each of the load cells 32, display the applied load, and output the load signal for digital data recording. A suitable load cell indicator is available from a variety of suppliers, including, for example, as the Model 3270 strain gage conditioner from Daytronic Corporation of Dayton, Ohio, which provides a regulated 10 VDC.

The digital acquisition hardware 36 is adapted to control both calibration and digital data recording of the test signal. The acquisition hardware 36 includes a connector block 38 which is attached to the data acquisition computer card 40 which is, in turn, operatively coupled with or incorporated into the computing device 42. A suitable connector block is the readily available BNC-2110; a suitable data acquisition computer card is available from a variety of suppliers, including, for example, as the PCI-MIO-16XE-50 data acquisition computer card from National Instruments of Austin, Tex.

The computing device 42 is conventionally operable to store and execute the test software and to receive and report test data. Preferably, the computing device 42 is a substantially conventional personal computer (PC). The computing device 42 broadly includes a memory and a processor. The memory is operable to store the test software and the test data; the processor is operable to execute the test software and to receive the test data. A suitable PC is readily available from a variety of manufacturers and retailers.

The test software is stored in the memory and executed by the processor of the computing device 42. The test software is adapted to facilitate and control the testing process by, for example, substantially controlling calibration of the testing system 10 via a user interface 104 (see FIG. 7) described below; controlling the forces applied and measurements made by the drive mechanism 22, measuring devices (e.g., the laser micrometers 28A, 28B), and other components of the testing system 10; and acquiring test data via the connector block 38 and the data acquisition computer card 40. The test software also functions to communicate or report various test parameters or results, including, for example, stress, strain, test time, maximum stress along, and two-dimensional X-Y or three-dimensional X-Y-Z plots of the test data in real time mode. Suitable "virtual instrument" computer programs can be generated using LabVIEW 5.1 programming tools or other software, and may include a spreadsheet to aid in data reduction.

Figure 5:
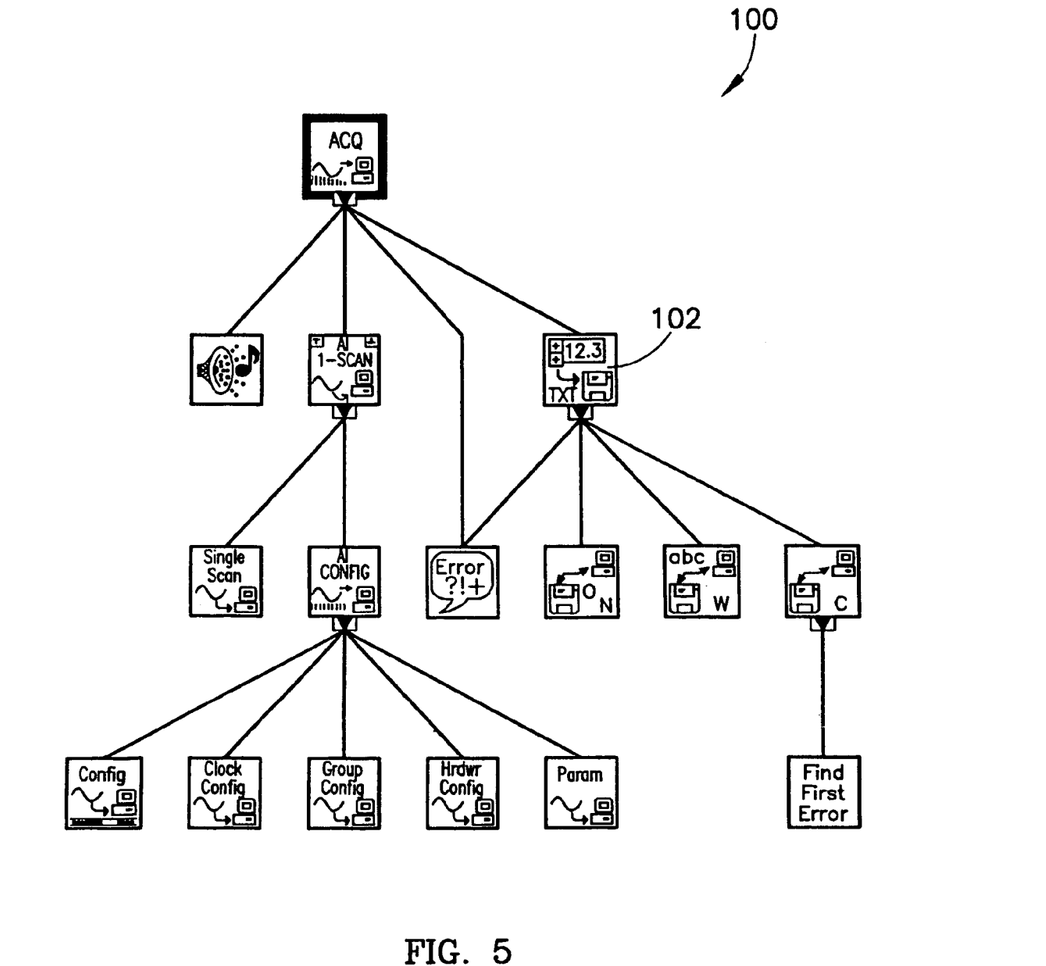
FIG. 5 is a block diagram showing an exemplary computer program that controls a data acquisition portion of a testing process performed using the testing system of FIG. 1.
Figure 6:
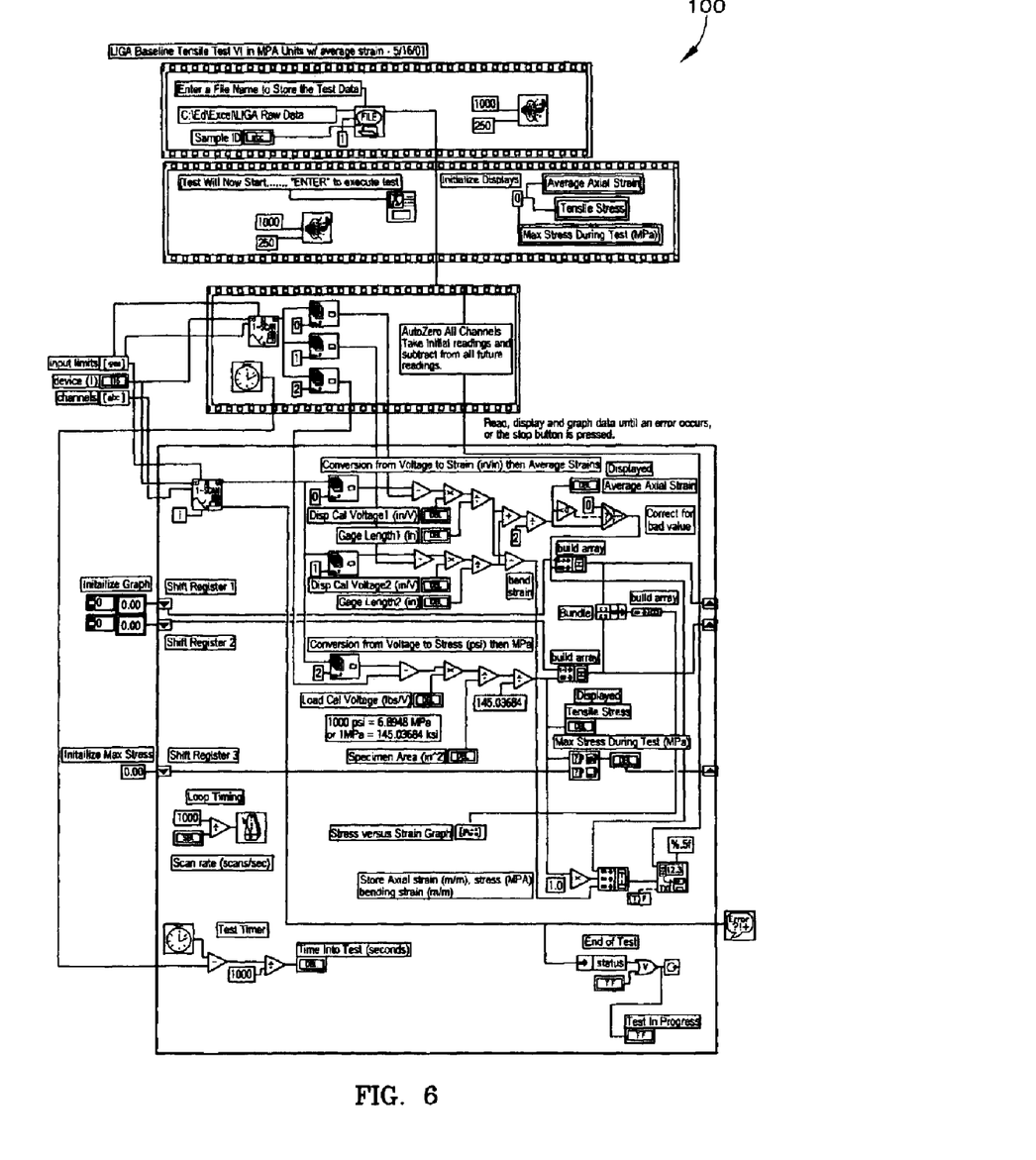
FIG. 6 is a detailed graphical depiction of a measurement portion of the computer program of FIG. 5.

Referring to FIG. 5, for example, a block diagram of LabVIEW 5.1 files is shown for one possible implementation of a computer program 100 that controls the data acquisition portion of the testing process. Of particular note is a write block 102 that causes the computer program to write test results to the aforementioned spreadsheet program. Referring also to FIG. 6, a more detailed LabVIEW 5.1 graphical depiction is shown of the computer program 100 of FIG. 5.

Figure 7:
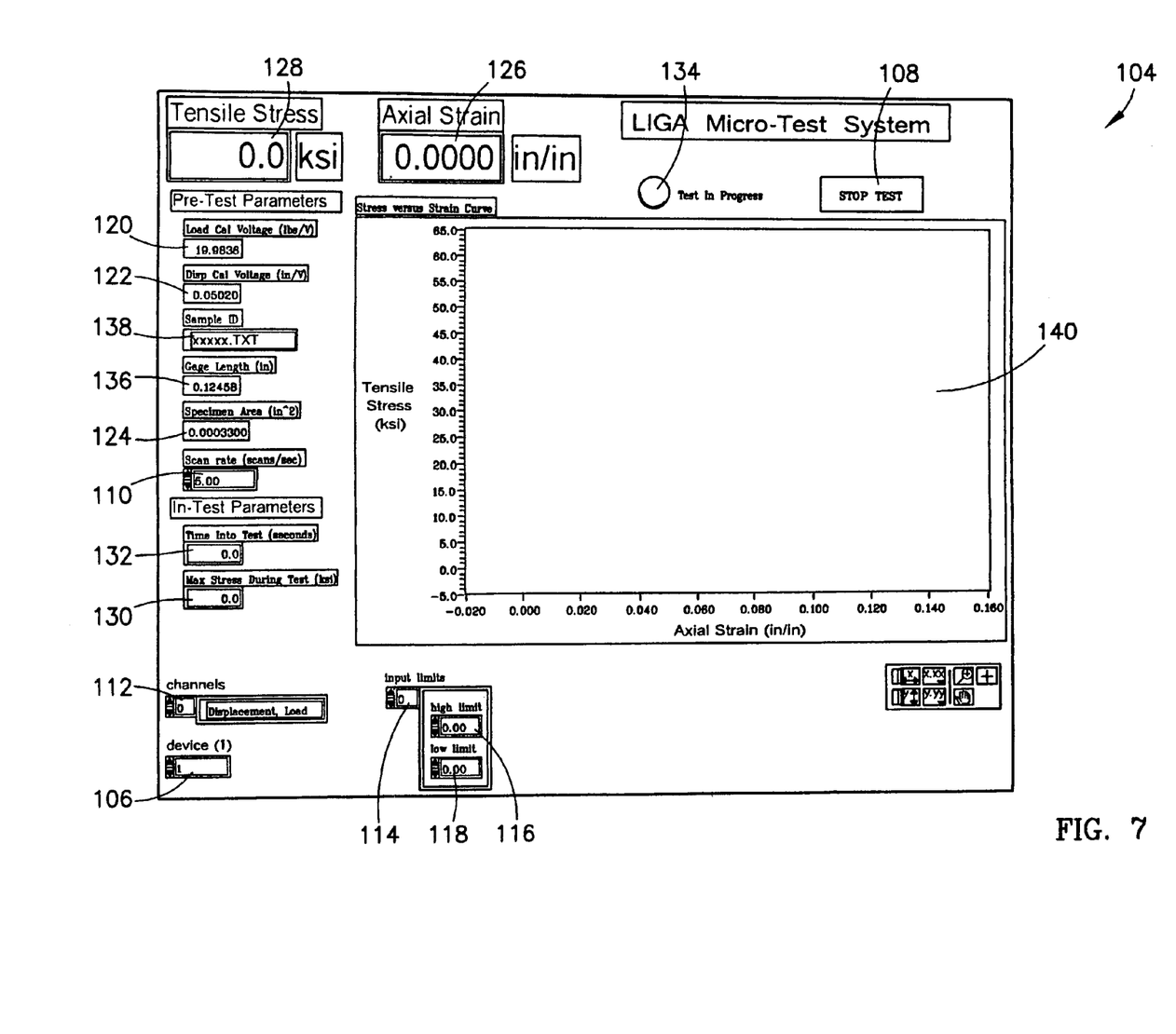
FIG. 7 is a screen display of a computer-generated user interface for controlling the testing process.

Referring also to FIG. 7, a screen display is shown of the above-mentioned exemplary front panel or user interface 104 generated by the computer program 100 of FIG. 5 and useful for controlling the testing process. In this example, the user interface 104 presents a number of relevant fields, including:

Device 106 number of particular device connected to data acquisition computer card 40 when data acquisition computer card 40 was configured;
Stop Test 108 selectable to stop execution of computer program;
Scan Rate 110 number of scans of all listed channels per second (scans/sec.);
Channels 112 analog input channels to be sampled with each scan (e.g., load, strain1, strain2);
Input Limits 114 input limit settings defining measurement ranges for channels selected in channels 112 field;
High Limit 116 upper limit of input measurement range;
Low Limit 118 lower limit of input measurement range;
Load Cal Voltage 120 load calibration voltage (lbs/V);
Disp Cal Voltage 122 displacement calibration voltage (in/V);
Specimen Area 124 dimensional area of test sample 11 ($in^2$);
Axial Strain 126 average axial strain measured during test (in/in);
Tensile Stress 128 tensile stress measured during test (ksi);
Max Stress 130 maximum stress measured during test (ksi);
Time Into Test 132 time from start of test (seconds);
Test In Progress 134 indicates test is in progress;
Gage Length 136 gage length of test sample 11 (in); and
Sample ID 138 data file name for storing test data.

The user interface 104 also presents a plot 140 of tensile stress (ksi) versus axial strain (in/in). It will be appreciated that the computer program, particularly the front panel, is readily customizable for specific applications, tests, and measurements of interest.

In operation, the testing system 10 functions as follows to determine or measure and report physical or engineering properties of the test sample 11. It will be appreciated that the order of performing some or all of these steps can be changed when appropriate. First, the test sample 11 is positioned and secured using the serrated grips 18A, 18B of the gripping supports 16A, 16B. If required or desired, the metal inserts or shims of the gripping supports 16A, 16B are changed to achieve alignment of the test sample 11 relative to the centerline of the frame 12, thereby advantageously ensuring an even load distribution on the frame 12.

Next, an appropriate one of the interchangeable load cells 32 is installed and then verified and calibrated using the load cell indicator.

Then, data concerning the testing sample 11 is entered into the user interface 104 generated by the computer program 100 stored on and executed by the computing device 42. The data includes, for example, the gage lengths for both sides of the testing sample 11 and the specimen area of the testing sample 11.

Next, as appropriate, calibrations of certain components (e.g., the laser micrometers 28A, 28B) of the testing system 10 are performed automatically by the computer program 100 or by the user using the user interface 104.

Thereafter, the test regime is initiated from the user interface 104, causing the computer program 100 to control the other components of the testing system 10 as various static, dynamic and cyclical tests are performed. As mentioned, such control includes, for example, controlling the test speed or displacement of the drive mechanism 22 from approximately between 0.0002 inches/minutes and 0.25 inches/minute, as required. The test speed is controlled by a simple internal program operable to provide multi-speed tests or any other type of programmed regime, including, for example, cycling tests and varying test profiles. The user can change the test speed during the test using the keypad 26.

In more detail, upon test initiation the computer program 100 starts the test clock (reflected in the Time Into Test 132 data field), lights the Test In Progress 134 indicator, and zeros all data channels. The program then proceeds to scan each channel in accordance with a loop timer. Data received via the channels is conditioned or processed in real-time to display and record, for example, the measured average strain and actual tensile stress. The test data is also presented in the plot 140 of tensile stress versus axial strain.

The test continues until the user stops the computer program 100 by selecting the Stop Test 108 button. The data file is then closed, storing the test data for post-test analysis. A printout is provided of the user interface 104 denoting the plot 140 of stress versus strain, the time into test, and the maximum stress experienced. A post-test analysis program can then used to process the stored data to calculate such parameters as Modulus of Elasticity, maximum engineering stress, 0.2% offset yield stress, and strain at failure.

From the preceding description, it will be appreciated that the testing system 10 of the present invention provides a number of substantial advantages over the prior art, including, for example, advantageously accommodating test samples 11 between approximately 0.0002 inch and 0.03 inch in size. Furthermore, the extreme rigidity of the frame 12 and the adjustability of the gripping supports 16A, 16B advantageously facilitates minimizing errors due to deflection and bending during testing. Additionally, the serrated grips 18A, 18B advantageously further facilitate securing the extremely small test samples during testing. Additionally, the laser micrometers 28A, 28B advantageously minimize measurement errors experienced by prior art testing systems using tangible extensometers. Additionally, integration of the testing software into the testing system 10 advantageously minimizes labor-intensive user work and user error by giving substantial control of calibration, testing, data acquisition, and data manipulation and analysis to the computer program 104.

Although the invention has been described with reference to the preferred embodiments illustrated in the attached drawings, it is noted that equivalents may be employed and substitutions made herein without departing from the scope of the invention as recited in the claims. For example, the particular computer program described herein may be adapted and customized as desired or required for specific applications, tests, and measurements of interest.

Having thus described the preferred embodiment of the invention, what is claimed as new and desired to be protected by Letters Patent includes the following:

1. A testing system for testing a property of a test sample of a material, the testing system comprising:
   a frame;
   a gripping support coupled with the frame and adapted to secure the test sample;
   a drive mechanism adapted to apply a load to the gripping support and the test sample;
   a microstepping drive coupled with the drive mechanism and operable to provide constant loading of the test sample to test tensile strength, the constant loading providing a generally uniform force per minute to the test sample;
   a laser micrometer adapted to measure as first test data a change in the test sample during testing; and
   a load cell having a value and adapted to record as second test data the load applied to the test sample during testing.

2. The testing system as set forth in claim 1, wherein the frame is adapted such that the test sample is alignable on the frame so that the load applied by the drive mechanism is substantially evenly distributed on the frame and wherein the frame is adapted to have a sufficient rigidity to allow for exerting up to approximately 250 pounds on the test sample with an error of approximately no greater than one percent.

3. The testing system as set forth in claim 1, wherein the gripping support includes an interchangeable metal insert that facilitates maintaining alignment of the test sample relative to a centerline of the frame so that the load applied by the drive mechanism is substantially evenly distributed on the frame.

4. The testing system as set forth in claim 1, wherein the drive mechanism includes an electric drive and a gearbox cooperating to provide both a desired degree of linear travel and control of a test speed, and further including a connecting rod extending between the gripping support and the drive mechanism and being adjustable to allow for accommodating a physical dimension of the test sample.

5. The testing system as set forth in claim 1, wherein the load cell is removable and replaceable with a different load cell having a different value.

6. The testing system as set forth in claim 5, wherein the value of the load cell is 25 pounds and the different value of the different load cell is 250 pounds.

7. The testing system as set forth in claim 1, further including a laser display monitor adapted to condition and display the first test data measured by the laser micrometer.

8. A testing system for testing a property of a test sample of a material, the testing system comprising:
   a frame;
   a gripping support coupled with the frame and adapted to secure the test sample;
   a drive mechanism adapted to apply a load to the gripping support and the test sample;
   a laser micrometer adapted to measure as first test data a change in the test sample during testing; and
   a plurality of load cells each having a different value associated therewith, a first load cell being adapted to record as second test data the load applied to the test sample during testing, wherein the first load cell is removable and replaceable with a second load cell.

9. The testing system as set forth in claim 8, wherein the frame is adapted such that the test sample is alignable on the frame so that the load applied by the drive mechanism is substantially evenly distributed on the frame and wherein the frame is adapted to have a sufficient rigidity to allow for exerting up to approximately 250 pounds on the test sample with an error of approximately no greater than one percent.

10. The testing system as set forth in claim 8, wherein the gripping support includes an interchangeable metal insert that facilitates maintaining alignment of the test sample relative to a centerline of the frame so that the load applied by the drive mechanism is substantially evenly distributed on the frame.

11. The testing system as set forth in claim 8, wherein the drive mechanism includes an electric drive and a gearbox cooperating to provide both a desired degree of linear travel and control of a test speed, and further including a connecting rod extending between the gripping support and the drive mechanism and being adjustable to allow for accommodating a physical dimension of the test sample.

12. The testing system as set forth in claim 8, wherein the value of the load cell is 25 pounds and the different value of the different load cell is 250 pounds.

13. The testing system as set forth in claim 8, further including a laser display monitor adapted to condition and display the first test data measured by the laser micrometer.

14. The testing system as set forth in claim 8, further including a microstepping drive coupled with the drive mechanism and operable to provide constant loading of the test sample to test tensile strength.

15. A testing system for testing a property of a test sample of a material, the testing system comprising:
   a frame;
   a gripping support coupled with the frame and adapted to secure the test sample, wherein the gripping support includes an interchangeable metal insert to facilitate alignment of the test sample on the frame;
   a drive mechanism adapted to apply a load to the gripping support and the test sample;
   a laser micrometer adapted to measure as first test data a change in the test sample during testing; and
   a load cell having a value and adapted to record as second test data the load applied to the test sample during testing.

16. The testing system as set forth in claim 15, wherein the frame is adapted such that the test sample is alignable on the frame so that the load applied by the drive mechanism is substantially evenly distributed on the frame and wherein the frame is adapted to have a sufficient rigidity to allow for exerting up to approximately 250 pounds on the test sample with an error of approximately no greater than one percent.

17. The testing system as set forth in claim 15, wherein the drive mechanism includes an electric drive and a gearbox cooperating to provide both a desired degree of linear travel and control of a test speed and further including a connecting rod extending between the gripping support and the drive mechanism and being adjustable to allow for accommodating a physical dimension of the test sample.

18. The testing system as set forth in claim 1, wherein the load cell is removable and replaceable with a different load cell having a different value.

19. The testing system as set forth in claim 18, wherein the value of the load cell is 25 pounds and the different value of the different load cell is 250 pounds.

20. The testing systems set forth in claim 15, further including a laser display monitor adapted to condition and display the first test data measured by the laser micrometer.

21. The testing system as set forth in claim 15, further including a microstepping drive coupled with the drive mechanism ad operable to provide constant loading of the test sample to test tensile strength.

22. A testing system for testing a property of a test sample of a material, the testing system comprising:
 a frame;
 a gripping support coupled with the frame and adapted to secure the test sample, wherein the gripping support includes an interchangeable metal insert to allow for further aligning the test sample on the frame;
 a drive mechanism adapted to apply a load to the gripping support and the test sample;
 a microstepping drive coupled with the drive mechanism and operable to provide constant loading of the test sample to test tensile strength, the constant loading providing a generally uniform force per minute to the test sample;
 a laser micrometer adapted to measure as first test data a change in the test sample during testing; and
 a plurality of load cells each having a different value associated therewith, a first load cell being adapted to record as second test data the load applied to the test sample during testing, wherein the first load cell is removable and replaceable with a second load cell.

* * * * *